United States Patent [19]

Lipschutz

[11] Patent Number: 4,761,740

[45] Date of Patent: Aug. 2, 1988

[54] COMBINED COLOR FLOW MAP AND MONOCHROME IMAGE

[75] Inventor: David Lipschutz, Lexington, Mass.

[73] Assignee: Hewlett-Packard Company, Palo Alto, Calif.

[21] Appl. No.: 837,456

[22] Filed: Mar. 7, 1986

[51] Int. Cl.[4] .............................................. A61B 10/00
[52] U.S. Cl. .................................. 364/415; 128/660; 358/81
[58] Field of Search ................ 364/415; 128/660, 663; 358/81, 82, 83

[56] References Cited

U.S. PATENT DOCUMENTS

| | | | |
|---|---|---|---|
| 4,205,687 | 6/1980 | White et al. | 128/663 |
| 4,584,880 | 4/1986 | Matzuk | 128/660 |
| 4,612,937 | 9/1986 | Miller | 128/663 |
| 4,641,668 | 2/1987 | Namekawa | 128/663 |

*Primary Examiner*—Jerry Smith
*Assistant Examiner*—Kimthanh Tbui
*Attorney, Agent, or Firm*—Donald N. Timbie

[57] ABSTRACT

A monochrome image of a cross-section of a body and a color representation of the velocity of blood flow therein are combined so that they are mutually exclusive by causing each pixel of a display to be in monochrome when a signal from which a velocity indicative signal may be derived is less than a minimum value or when that signal exceeds the minimum value and a weighted value of the velocity indicative signal is less than a weighted value of the signal for the monochrome image, and to be in color when the signal from which a velocity indicative signal may be derived exceeds the minimum value and a weighted value of a signal indicative of velocity exceeds a weighted value of the signal for the monochrome image.

1 Claim, 1 Drawing Sheet

COMBINED COLOR FLOW MAP AND MONOCHROME IMAGE

BACKGROUND OF THE INVENTION

Ultrasound apparatus has been described that forms an, image of structures within a body of a patient in monochrome and superimposes colors thereon that are intended to indicate the velocity of blood flow, e.g., see U.S. patent application Ser. No. 748,531, filed June 25, 1985 by David Lipschutz and entitled "Flow Mapping Apparatus". Ideally, the monochrome image would only represent structures other than blood, and the colors would only appear where the blood is flowing. For various reasons, however, color appears in structural areas where there is no blood. This is caused in part by the fact that some structures, like heart walls, are in motion so as to produce velocity signals that cause color to appear in the image. Because the velocity of such motion is less than the velocity of blood flow, it is possible to reduce this effect by using what is known as a "wall filter"; but because of fundamental limitations, it cannot operate perfectly. Even without such wall motion, however, electrical noise may cause false indications of velocity because the signals from which the velocity is determined are weak. Furthermore, combining the monochrome image representing structure with colors representing velocity of flow by simple addition causes the colors to be changed by desaturation in a manner that is completely unrelated to velocity.

BRIEF SUMMARY OF THE INVENTION

This invention makes it possible to form a monochrome image of structure and a color presentation of blood velocity that are mutually exclusive.

If the signals from which velocity is derived are less than some minimum level, only the monochrome image of structures within the body is displayed because reliable velocity estimates cannot be calculated from very small signals. This would occur at an amplitude that is less than the typical signal amplitude for blood flow in the heart.

If the signals from which velocity is derived are greater than the minimum, a weighted comparison is made between the amplitude of the monochrome signal and the amplitude of the actual calculated velocity. As the amplitude of the monochrome signal increases, it becomes less and less likely that a given pixel should be displayed in color corresponding to blood velocity, because the reflections from blood have a small amplitude. On the other hand, as the amplitude of the actual velocity signal increases, it becomes more and more likely that a given pixel should be displayed in a color related to blood velocity since the velocity of the motion of body structure like the heart wall is low.

A weighted comparison, as represented in the equation below, takes both effects into account.

(1) if $X*AM > Y*V$ display monochrome. If the left quantity is greater, a pixel is only displayed in monochrome.

The values of X and Y that are used depend on experience. By way of example, X can be made equal to $(1-W)$ and $Y=W$ in which W has values from 0 to 1. For values of W near 0, only significant velocities of blood flow that are within areas for which the monochrome signal is very weak will be displayed. For values of W near 1, color will begin to be displayed for pixels at the tops of heart valves and walls. For intermediate values of W, a good trade-off can be achieved with color displays in the chambers of the heart, but little if any color in the valves and walls.

BRIEF DESCRIPTION OF DRAWING

The sole drawing shows circutry for a comparison of images and velocity in mutually exclusive areas of the screen.

DETAILED DESCRIPTION OF THE INVENTION

Figure 1:
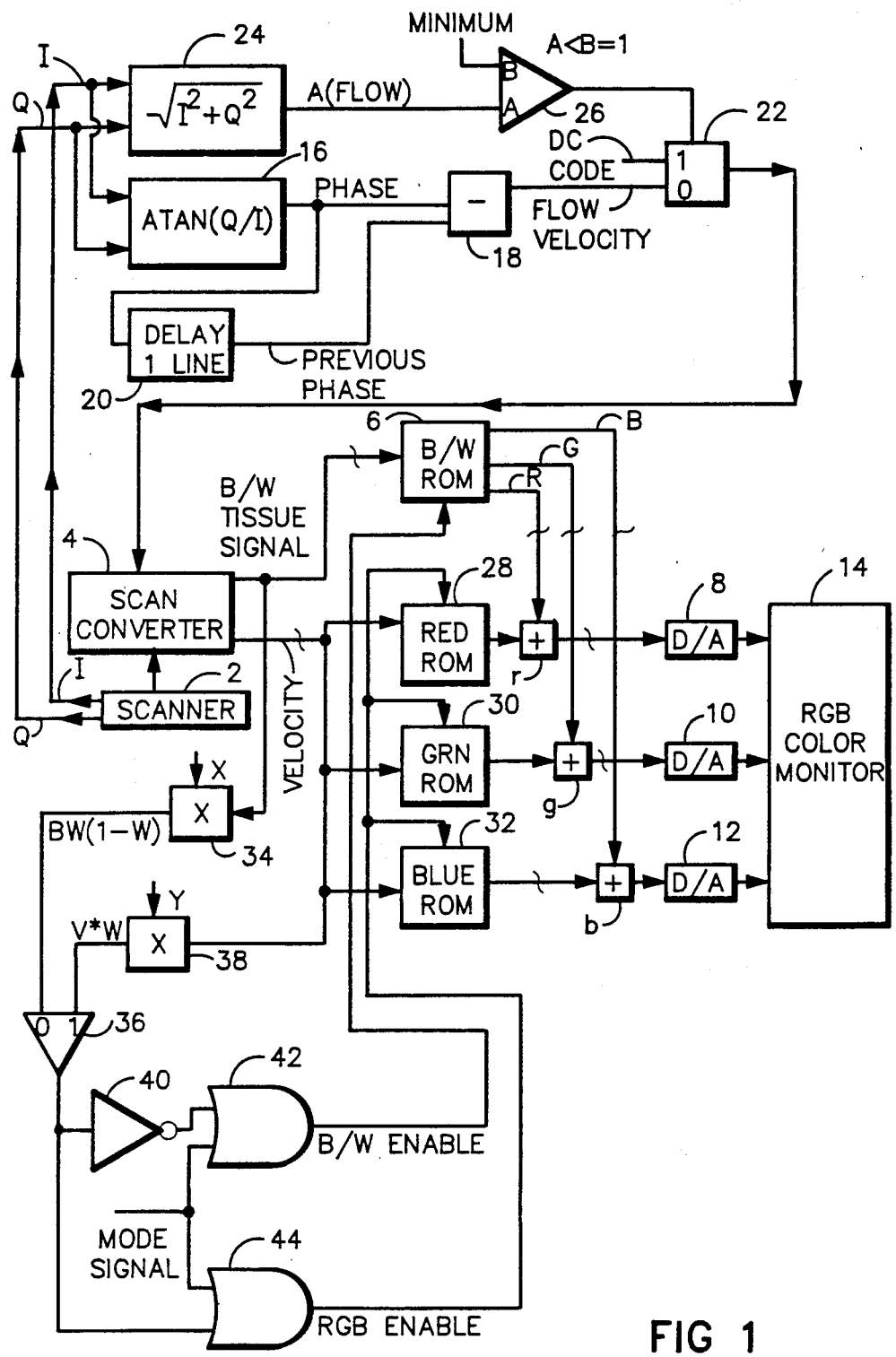

In the drawing, transducers, not shown, in a scanner 2 transmit pulses of ultrasound pressure waves along successive radial directions into the body of a patient. Reflections from structures along each radial line cause the transducers to produce analog electrical signals. An image of the structures could be formed by modulating the intensity of an electron beam of a cathode ray tube that is made to scan along corresponding radial lines, but it is generally preferred to form an image by modulating an electron beam that scans a series of parallel lines, as in television receivers. In order to do this, the analog signals for each radial line are sampled at uniformly spaced intervals by an A/D converter, not shown, and applied to a scan converter 4. In a manner described in U.S. Pat. No. 4,471,449 issued on Sept. 11, 1984 and assigned to Hewlett-Packard Company, the intensity modulation tissue signal for each pixel in the parallel raster line display is derived by interpolating samples that surround it. These signals are applied to a ROM 6 that outputs signals that can be respectively applied via adders r, g and b and via respective D/A devices 8, 10 and 12 to the R, G and B intensity control electrodes of a color cathode ray tube, not shown, in a color monitor 14 so as to form a monochrome image.

The scanner 2 also samples the electrical signals produced by the transducers at 90° points of the frequency of the waves transmitted into the body so as to derive what is known as I and Q signals. A circuit 16 derives from the I and Q signals the arc tangent of Q/I so as to derive a signal indicative of phase. This signal is applied directly to one input of a subtractor 18 and indirectly to another input thereof via a delay 20 equal to the time between successive acoustic pulses. By noting the change in phase occurring between adjacent ones of a number of pulses, a signal corresponding to the average frequency of the reflected acoustic waves can be derived and can be used to represent velocity even though it is not the velocity itself. This signal is applied to the zero input of a switch 22.

By deriving the square root of the sum of $I^2$ and $Q^2$, a device 24 derives a signal corresponding to their vector sum. It is important to note that this is different from the phase difference representing velocity that is derived in a manner described above. The vector sum is compared by a comparator 26 with a signal that experience indicates to be the minimum value that will yield reliable estimates of phase difference. If the amplitude exceeds the minimum, the comparator 26 outputs a "0" to the switch 22 so as to cause it to pass the velocity signal to its output; but if the signal is less than the minimum, a DC CODE value corresponding to zero velocity is passed to the output of the switch 22.

The output of the switch 22 is shown as being connected to the scan converter 4 but, in actuality, it is an entirely separate scan converter that operates in the same way as previously described to derive a signal representing velocity for each pixel in the final display. As described in U.S. patent application Ser. No. 748,531 filed on June 25, 1985 for David Lipschutz and entitled "Flow Mapping Apparatus", the signal representing velocity may be applied to ROMs 28, 30 and 32 that respectively control the relative intensities and hue of the color for each pixel. The outputs of the ROMs 28, 30 and 32 are respectively applied via the adders r, g and b and the D/A devices 8, 10 and 12 to intensity control electrodes for the R, G and B colors.

The tissue signal at the output of the scan converter 4 is applied to a multiplier 34 wherein it is multiplied by a weighting factor X, and the output of the multiplier 34 is applied to one input of a comparator 36. The phase signal at the output of the scan converter 4 that represents velocity is applied to a multiplier 38 wherein it is multiplied by a weighting factor Y, and the output of the multiplier 38 is applied to the other input of the comparator 36. The output of the comparator 36 is applied via an inverter 40 to one input of an OR gate 42 and directly to one input of an OR gate 44. A mode signal may be applied to the other inputs of the OR gates 42 and 44. The output of the OR gate 42 is applied to an enabling input of the ROM 6, and the output of the OR gate 44 is applied to the enabling inputs of the ROMs 28, 30 and 32.

If the weighted tissue signal BW is $(1-W)$ is greater than the weighted velocty-representing signal VW, the output of the comparator 36 will be a "0" that is inverted by the OR gate 42 so as to enable the BW ROM 6 to output the R, G and B signals required to produce a monochrome image of the correct intensity; but if the BW $(1-W)$ signal is less than the VW signal, the output of the comparator 36 will be a "1" so as to cause the OR gate 44 to enable the color ROMs 28, 30 and 32. This assumes a mode signal of logic level "0". Thus, each pixel on the screen of the monitor 14 is either at a monochrome intensity for an image or at a hue and intensity of color related to the velocity of blood flow. Thus, if it is desired to have the monochrome image and the colored flow map representing blood flow superimposed, as in my aforesaid patent application, the mode signal is set to a logic "1".

What is claimed is:

1. Ultrasonic apparatus for forming an image in which body tissue is displayed in monochrome and the velocity of blood flow is displayed in color, said apparatus comprising means for providing a first signal that varies in amplitude with the amplitude of reflections of acoustic pulses tansmitted into the body of a patient by tissue and blood in the body, means for deriving a second signal from reflections of acoustic pulses transmitted into the body of a patient that can be used to provide a third signal indicative of the velocity of blood and tissue therein, means for deriving said third signal from said second signal, a monitor, means for causing said monitor to produce monochrome light in response to said first signal when said second signal is less than a given minimum amplitude or when said second signal is greater than said given minimum amplitude and a weighted value of said first signal is greater than a weighted value of said third signal, and means for causing said monitor to produce colored light related to the value of said third signal when the amplitude of said second signal exceeds said given minimum value and a weighted value of said third signal is greater than a weighted value of said first signal.

* * * * *